United States Patent [19]

Brennan

[11] Patent Number: 4,941,875
[45] Date of Patent: Jul. 17, 1990

[54] I.V. SYSTEM FOR SUCCESSIVE ADMINISTRATION OF TWO OR MORE SOLUTIONS AT DIFFERENT RATES

[76] Inventor: John F. Brennan, 14476 Harbor Island, Detroit, Mich. 48215

[21] Appl. No.: 58,725

[22] Filed: Jul. 18, 1979

[51] Int. Cl.$^5$ .............................................. A61M 5/00
[52] U.S. Cl. ...................................... 604/81; 604/126; 604/83
[58] Field of Search ............... 128/213, 214 R, 214 C, 128/214.2, 227, 214 G; 137/112–114; 222/129.2, 145; 604/80–86, 122–126

[56] References Cited

U.S. PATENT DOCUMENTS

| | | | |
|---|---|---|---|
| 2,850,211 | 9/1958 | Fernandez | 128/214 R X |
| 2,999,499 | 9/1961 | Willet | 128/214 R |
| 3,216,419 | 11/1965 | Scislowicz | 128/272 X |
| 3,738,361 | 6/1973 | Price | 128/214 E |
| 3,886,937 | 6/1975 | Bobo et al. | 128/214 G |
| 3,982,534 | 9/1976 | Buckman | 128/214 G |
| 4,031,891 | 6/1977 | Jess | 128/214 R |
| 4,034,754 | 7/1977 | Virag | 128/214 G |
| 4,055,176 | 10/1977 | Lundquist | 128/214 C |
| 4,116,646 | 9/1978 | Edwards | 128/214 R |
| 4,219,022 | 8/1980 | Genese | 128/214 G |
| 4,256,104 | 3/1981 | Muetterties et al. | 128/214 G |
| 4,258,712 | 3/1981 | Harms et al. | 128/214 G |

Primary Examiner—Dalton L. Truluck

[57] ABSTRACT

The intravenous (I.V.) system provides for successive administration to a patient of two or more solutions but at different flow rates. Such system includes a primary or first intravenous set including tubing which at one end thereof enters a container having a first solution at a predetermined level and which extends from that point towards the patient. The tubing of the primary set includes a check valve above the connector site. A secondary set may be temporarily or permanently connected to the connector site and includes tubing attached to a second container having a second solution at a level above the level of the first fluid. Adjustable and independent flow control devices are provided in the tubing of the primary set, one flow control device being located downstream of the connector site for controlling the flow of solution from the second container and the other flow control device being located upstream of the connector site for automatically turning on and off the first solution at its own, individually set, flow rate, generally after the termination of the flow of the solution from the second container.

45 Claims, 2 Drawing Sheets

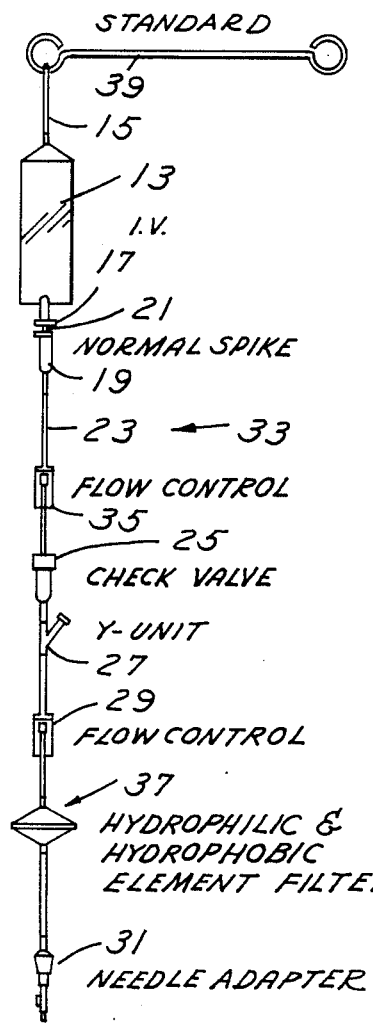
FIG. 2
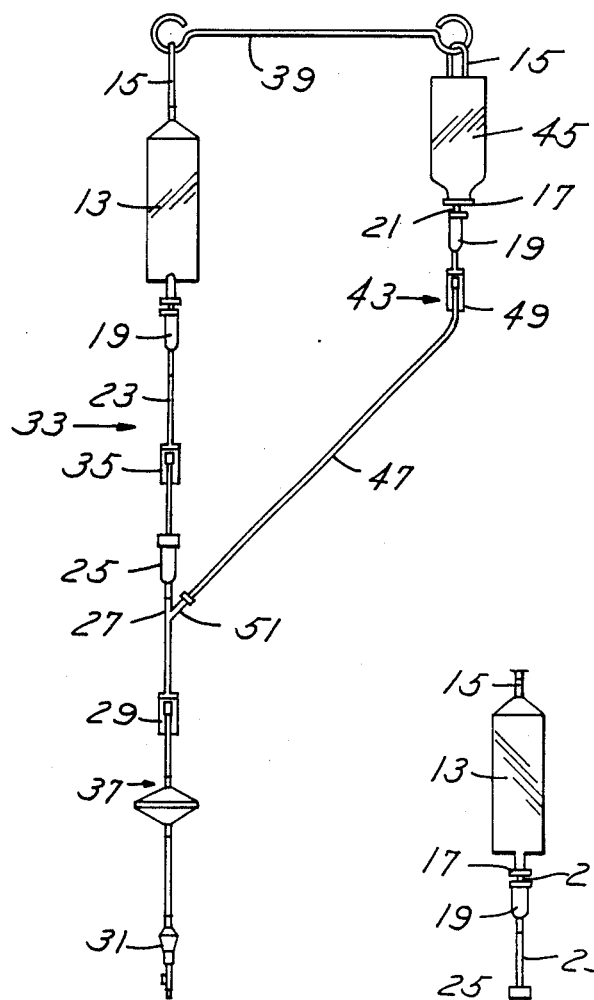
FIG. 3
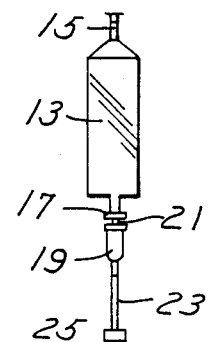
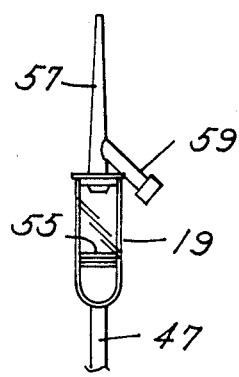
FIG. 5
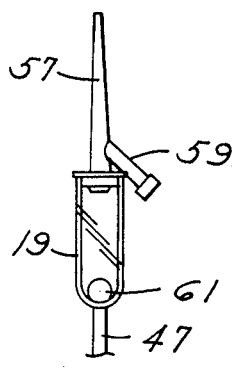
FIG. 6
PRIOR ART
FIG. 1

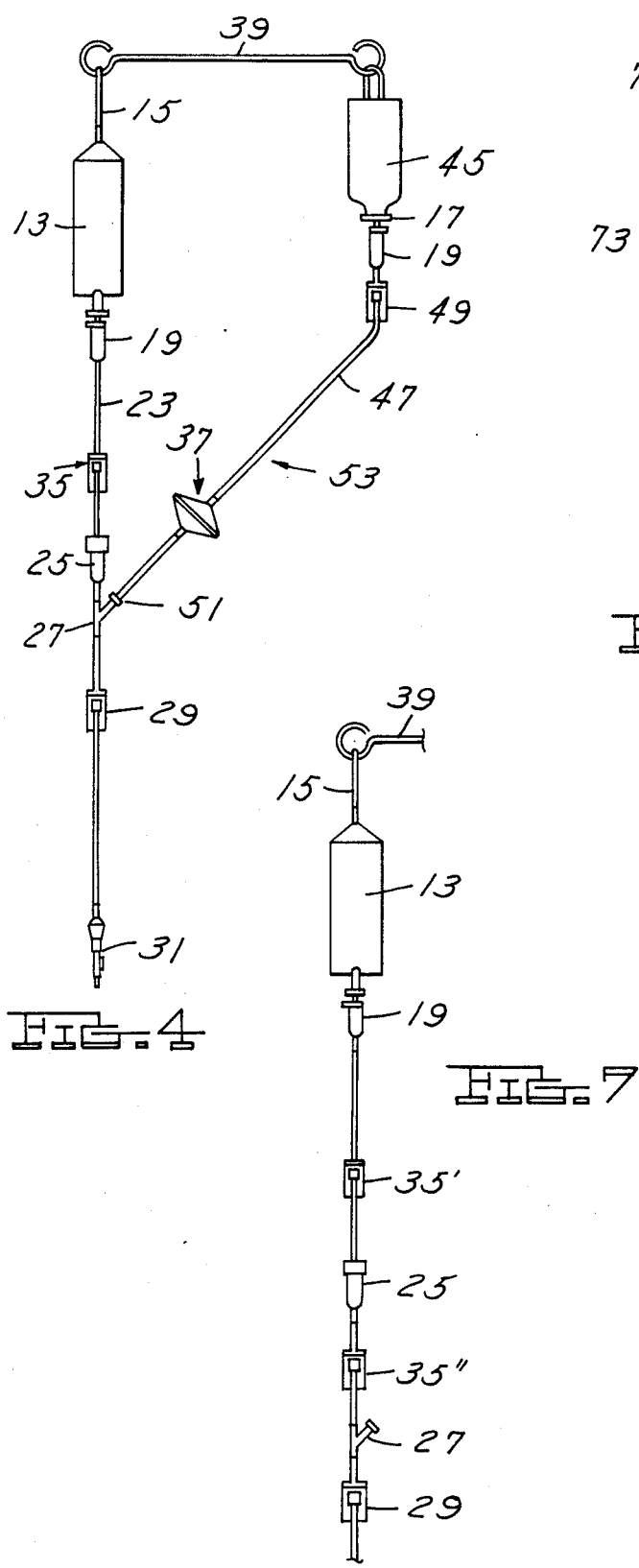
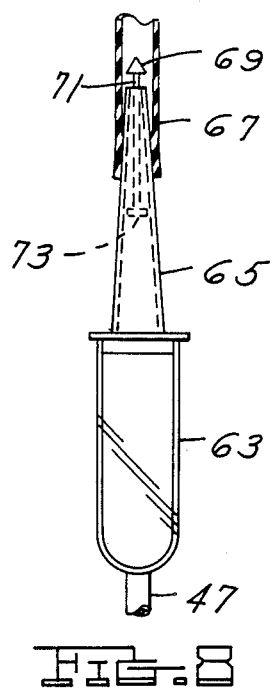

//  4,941,875

I.V. SYSTEM FOR SUCCESSIVE ADMINISTRATION OF TWO OR MORE SOLUTIONS AT DIFFERENT RATES

BACKGROUND OF THE INVENTION

At this time all the major intravenous set manufacturers make and market intravenous administration sets which allow the addition of a second solution via a second intravenous set which automatically stops the flow of the primary set by the use of a check valve in the primary set when the fluid level of the second solution is higher than the first solution.

At the point where the second solution level is drained to the level of the first solution, the check valve opens and the first solution begins to run but at the same rate as was set for the second solution. This is because both solutions must be regulated by the same flow restriction or control device which must be below the place where the two sets join in order to eliminate the potential of drawing air into the line.

As in the majority of instances, the secondary set rate is higher, flowing faster, than the first (primary or keep open) set rate, this necessitates the nurse or attendant returning and resetting the flow rate after the second solution has run out. Failure to do this can lead to very serious complications or death to critically ill individuals. Adjustable flow control clamps or devices have been used in connectionn with intravenous sets and are assembled onto the usually transparent plastic tubing for controlling the flow rate therethrough. An example of such flow control clamp is shown in U.S. Pat. No. 3,685,787. Such clamp includes a movable element which operatively engages a wall of the tubing for leaving it fully open or progressively reducing its cross sectional area to the point of closing off all flow. Other types of flow control clamps may be used as is well known in the art such as roller clamps, slide clamps, screw clamps and other flow control devices.

Conventional intravenous sets normally utilize a check valve in the primary tubing above the connector site responsive to pressure by which if the secondary solution is maintained at a level above the level of the primary solution, during the flow of the secondary solution into and through the connector site the check valve is effective to cut off all flow of the primary solution.

Heretofore, in the application of a secondary solution by the usual Y-connector site into the primary intravenous set, close attention is required by the nurse or operator so that once the secondary solution has been exhausted the conduit therefor will be closed off to prevent the accidental introduction of air into the primary intravenous set.

SUMMARY OF THE INVENTION

In order to allow the first or primary set to automatically restart or to begin flow of the first solution at the proper rate the standard combination intravenous sets are modified in several respects, first by the application of a filter which is placed in the tubing below the joining point of the first and second sets. The filter will be a dual filter having a hydrophilic element and a hydrophobic element respectively, i.e., a hydrophilic element covers the fluid path and allows the passage of fluids only and the hydrophobic filter element allows only the passage of air but no fluids, the air being vented to atmosphere from the filter chamber. The placement of the proposed dual filter can be either above or below the usual flow control device which is located below the connector site.

Above the connector site which forms the joining point of the primary and secondary set another manually adjustable flow control device is placed in the tubing of the primary set in order to regulate the flow of the first solution. This flow control device is normally placed above or below the check valve actuated by hydraulic pressure. This allows the primary or first solution to be regulated by its own flow control device above the joining of the two conduits. Therefore if the rate of flow of the second solution is faster than the flow rate of the first solution it is controlled by the basic flow control device in the primary set below the joining point or connector site. When the secondary solution level equalizes the primary solution, the primary solution will restart or begin at its original preset and controlled rate as set above the joining point. Any air if it enters the set, will come through the now empty secondary intravenous set and will be eliminated in the dual element filter. It is a further object to provide a modified alternate intravenous set arrangement wherein some form of filter element or valving device is incorporated into the second intravenous set which would allow the passage of fluids only and stop the passage of air. The chamber can be air venting or not and the filter can be placed anywhere in the secondary set.

A modified secondary intravenous set includes the hydrophilic filter nested within the drip chamber of the secondary set or alternately there may be an air control ball check floatable valve within the drip chamber of the secondary set to prevent the passage of air therethrough when the supply of fluid is exhausted. A further modification includes within the secondary set a positive air control valve incorporating a slide mounting and a float normally immersed within the fluid and adapted to automatically close when the fluid lowers to a predetermined level.

These and other objects will be seen from the following Specification and Claims in conjunction with the appended drawings in which:

THE DRAWINGS

FIG. 1 is a front elevational schematic view of the prior art I.V. assembly.

FIG. 2 is a similar view of the present improved I.V. set including a Y-connector unit or connector site adapted for the connection thereto of a second I.V. set.

FIG. 3 is a view similar to FIG. 2 showing the application of the second I.V. set thereto.

FIG. 4 is a similar view of the I.V. set shown in FIG. 3 with the dual purpose filter arranged within the secondary tubing.

FIG. 5 is a fragmentary view on an enlarged scale of the drip chamber of the secondary set with a modified hydrophilic filter within the drip chamber therefor.

FIG. 6 is a fragmentary view of the drip chamber for the secondary set shown in FIG. 4 showing an air control ball check valve.

FIG. 7 is a fragmentary schematic view of an I.V. set generally in accordance with FIG. 2 and showing alternate locations of the flow control devices.

FIG. 8 is a fragmentary view on an increased scale of the drip chamber for the secondary I.V. set of FIG. 3 showing a positive normally open air control valve and associated float.

DETAILED DESCRIPTION OF THE INVENTION

Referring to the drawings, the conventional intravenous or I.V. set of the prior art is shown in FIG. 1 generally indicated at 11 including solution container 13, in the form of a bag or bottle, with loop or hanger 15 adapted for suspension from a conventional standard. The container 13 at its inverted lower end has a conventional pierceable closure stopper 17. Drip chamber 19 at its upper end includes an elongated hollow connector spike 21 which may be vented or unvented and which is adapted for projection into and sealing within the stopper 17 for communication with the solution within the container 13. A conventional transparent plastic tubing or conduit 23 depends from the drip chamber 19 in communication therewith and incorporates a pressure operated check valve 25 and therebelow has a connector site or Y-connector site 27 adapted for the connection thereto of a secondary intravenous set. A manually adjustable flow control clamp or device 29 is applied to the conduit 23 and, as an example, is of a construction such as shown in U.S. Pat. No. 3,685,787. The device 29 is adapted to apply pressure to a wall of the tubing so as to permit full flow of solutions therethrough throughout the full cross sectional area thereof or for pressing into and reducing the cross sectional area of the passage to some intermediate condition or for fully closing off flow through the tubing or conduit 23. The plastic tubing 23 at its other end terminates in a needle adapter 31 adapted for the reception of a conventional solution delivering needle which is introduced into the patient's vein all in a conventional manner. Other types of flow control devices 29 may be used such as roller clamps, slide clamps, screw clamps as is well known in the art. The foregoing is a conventional construction.

In such conventional construction provision is made for the addition of a secondary solution via a second intravenous or I.V. set whose flexible conduit is connected temporarily by a needle or permanently by some other connection directly into the Y-connection site such as shown at 27. The pressure operated check valve 25 functions so that when the secondary solution is held at a head or level above the primary solution the flow of the solution from container 13 is stopped until either the flow from the secondary solution is exhausted or drops to a level equal to the level of the solution in container 13. When the secondary solution is drained to such level, check valve 25 opens and the first solution in container 13 begins to run, but at the same rate as was set for the second solution employing the conventional manually operated flow control device 29, FIG. 1. Heretofore, both solutions were controlled by the single flow control device 29 which had to be placed below the place where the two sets joined in order to eliminate the potential of drawing air into the line once the secondary solution had been exhausted. Normally the flow from the secondary set is at a rate which is higher and flows faster than the first set or keep open set. This necessitates that the nurse must return and reset the flow rate of the flow control device 29 after the second solution from the second set has run out.

FIG. 2 schematically illustrates the present improved I.V. set or primary set designated at 33 as a first embodiment and which includes a number of the parts heretofore described with respect to the prior art I.V. set in FIG. 1. The numbers are the same and the description thereof is not repeated.

In the primary set 33 container 13 is suspended from an adjustable I.V. stand 39 or similar device well known in the art. Such device normally rests upon the floor or can be clamped to a bed frame or it can hang from the ceiling. The primary set 33 includes the above described drip chamber 19 and connector or spike 21, the depending preferably transparent flexible plastic tubing 23, a check valve 25, the Y-connector site at 27, manually operated flow control clamp 29 and the needle adapter 31.

The present improvement incorporates into tubing 23 a second manually adjustable flow control clamp or device 35 which is interposed upon the tubing 23 above the Y-connector site 27. Accordingly, one problem heretofore experienced with the construction of FIG. 1 is overcome namely, the fact that flow of the primary set 33 will be at a predetermined rate of flow due to the presetting and adjustment of the flow control clamp 35 above the Y-connection site 27. The conventional adjustable flow control device 29 is preset for controlling the flow of the secondary I.V. set solution at the faster rate. When that flow is discontinued or is stopped the flow of the primary solution from container 13 is automatically controlled at its own preset rate by virtue of the introduction of the manual flow control device 35 which was not present in the prior art construction, FIG. 1.

Another improvement shown in FIG. 2 is the introduction of a dual filter 37 into the conduit or tubing 23 below the Y-connection site 27 primarily adapted for the filtration of all liquids passing therethrough. The dual filter 37 of FIG. 2 is referred to as including a hydrophilic element controlling the passage of liquids only and a hydrophobic element vented to atmosphere for controlling the passage of air only. By this construction once the solution in the secondary I.V. set has been exhausted or has stopped and the primary solution restarted automatically and at the rate preset by the flow control device 35, the dual filter 37 prevents passage of any atmospheric air within the empty second solution container such as shown at 45, FIG. 3, from going into the system or set 33 to the needle adapter 31. The primary set 33 is, as an example, suspended from the conventional hanger 15 carried by a conventional stand or standard 39. Instead of using a dual element filter 37, a single hydrophilic element may be used.

Another embodiment of the invention FIG. 3, includes the application to the standard 39 of a secondary intravenous or I.V. set generally indicated at 43 and wherein the container 45 containing a second solution is suspended by hanger 15 from the standard 39 and includes the conventional pierceable stopper 17. Depending therefrom is a conventional drip chamber 19 having a conventional connector spike 21 which is projected up through the stopper 17 for communication with the fluid within container 45. A second transparent plastic tubing or conduit 47 depends from drip chamber 19 and at one end as at 51 is connected into the Y-connector site 27. This connection can be made permanent by projecting the plastic tubing 47 into the Y-connector site 27 and securing therein as by cementing or alternately the end of the tubing 47 may have a needle adapter with the needle therein projected into the connector site 27 and sealed therein.

The embodiment shown in FIG. 3 is therefore the adaptation of the second intravenous or I.V. set 43 to the primary I.V. set 33 of FIG. 2. The pressure head of the fluid within the second container 45 is greater than the head within the container 13 of the first I.V. set 33. This is achieved with the level of the fluid within container 45 above the level of the fluid within container 13. The hanger 15 is used to lower the level of the primary solution as it relates to the secondary solution in order to provide the difference in head pressure. Various types of standards or hangers may be used as is well known in the art.

In the operation of the secondary I.V. set 43 in conjunction with the first set 33 as in FIG. 3 (which first set corresponds to the set shown at 33, FIG. 2,) due to the action of the check valve 25, initiating of flow of the secondary solution from container 45 at an increased pressure head stops the flow of any fluid through conduit or tubing 23 and through the check valve 25 until the fluid in container 45 is exhausted or at least reaches a level equal to the level of the fluid in container 13.

Primarily the problem is the prevention of the entry of air from the exhausted secondary I.V. set 43. This is accomplished by the use of the dual purpose hydrophilic/hydrophobic filter 37 arranged in the conduit 23 below the Y-connector site 27. Accordingly, when the flow from the secondary solution stops, its rate of flow being controlled by clamp 29, the check valve 25 opens and the flow from the container 13 automatically restarts but at a rate preset by the manually controlled adjustable clamp or device 35. A third flow control clamp 49 is normally left wide open although the configuration of FIG. 3 will allow the simultaneous administration of two fluids at independently controlled rates.

A modified intravenous or I.V. set is shown in FIG. 4 which incorporates the primary set 33 of FIG. 2 and the secondary set 43 of FIG. 3 however the dual purpose hydrophilic/hydrophobic filter assembly 37 has been removed from the main primary tubing 23 and introduced into the secondary tubing 47 intermediate its ends in the set arrangement shown at 53 (FIG. 4).

Since an important problem is the prevention of the entry of air from the secondary I.V. set, the location of the dual purpose filter arrangement at 37 accomplishes this result. At the same time the flow from the respective sets is individually controlled in the primary set 33 by the manually adjustable clamp or device 35, and by the manually adjustable clamp 29. As mentioned previously the third flow control device 49 in the second tubing 47 is manually wide open or is manually adjusted to permit administration of two fluids at the same time. At such time flow control devices 35 and 49 are adjusted and flow control device 29 is set wide open.

A further modified I.V. set is shown in FIG. 5 which is a fragmentary view showing a change in the drip chamber 19 connected with the secondary container 45, shown on an increased scale and wherein instead of the dual filter at 37, FIG. 4, there is merely provided a spike connector 57 upon the drip chamber 19 for projection within the stopper 17 of container 45 and which may have an air vent at 59. A hydrophilic filter element is shown at 55 nested within drip chamber 19 for the filtration of liquid passing therethrough.

A further modification is schematically shown in FIG. 6 in place of the dual filter arrangement at 37, FIG. 4, and wherein here the drip chamber 19 and the associated connector or spike 57 vented at 59 has instead of the filter 55, the positive ball check float valve 61. By this construction when the liquid from the second container 45 within drip chamber 19 reaches the bottom thereof, ball check 61 will close the conduit 47 to prevent the passage of any atmospheric air thereinto.

A modification of the air control device is further shown in FIG. 8 wherein the corresponding drip chamber shown on an increased scale at 63 has a hollow connector spike 65 normally filled with the solution from container 45 which projects into the stopper outlet 67 and is sealed therein.

Air valve closure tip 69 is normally spaced above the top of connector 65 to permit the passage of solution from container 45 into the drip chamber 63 and out the conduit 47, fragmentarily shown. Air valve closure tip 69 is mounted upon the upper end of slide 71 which loosely and slidably extends through the outlet end of the connector 65 and at its lower end mounts a float 73. The float 73 is normally movably positioned within the fluid within the connector for holding the air valve 69 open as shown in FIG. 8. Once the level of the solution within container 65 falls to a predetermined point, the float 73 will correspondingly fall so that the air valve closure tip 69 seats over the upper end of the connector 65 and prevents the passage of air from the secondary container 45 down into drip chamber 63.

The spike 65 including its air control system or device is an alternative system which can be used as described in place of the dual filter 37 of FIG. 4. Also the air control systems of FIGS. 5 and 6 can also be used as described in place of the dual filter 37 of FIG. 4. Such alternate air control devices of FIGS. 5, 6 and 8 may be used (but are not necessary to the functioning of the system), in conjunction with the system or set shown in FIG. 2 and thereby provide an additional margin of safety. The only air control system required in FIG. 3 is the dual filter 37.

In the embodiment of FIG. 7, the Y-site connector 27 must be located below the check valve device 25. The second or new flow control device 35 can be located above the check valve device 25 as shown by 35' or located below the check valve device 25 as shown by 35". In each instance however the new flow control device 35' or 35" must be located above the Y-connector site 27 where the secondary solution is added. The flow control device 29 controls the rate of flow of the second solution from a secondary set connected to the connector site 27.

The Y-site 27 used to connect the secondary tubing must be located below the flow control clamp 35 which controls the primary rate. The check valve 25 in the primary set must be above the Y-site 27 where the secondary set is connected. The flow control clamp 35 for the primary set may be above or below the check valve 25 but always above the Y-site 27 where the secondary set is to be connected. As a term of current art, an I.V. set is the tubing which at one end enters the I.V. container (bottle or bag) and extends from that point towards the patient. Some sets go all the way to the needle adapter like the primary set in the described system, some only to a site on the set like the secondary set. Extension sets may go from a set to the patient or another set. Some sets go to or from pumps or pump cassettes which form flow control devices.

The present invention includes any single set or combination of sets which will accomplish the independent flow control of the primary and secondary solutions and automatically turn off and on the primary solution at its own, individually set, flow rate.

With reference to the embodiment of the invention shown at 53, FIG. 4, while this has been described as a dual filter element, this filter element could be merely a hydrophilic filter for the filtration of liquids through the conduit 47. The various embodiments described with respect to FIGS. 5, 6 and 8 could be employed within the secondary intravenous or I.V. set 43 to prevent the passage of air through the conduit 47 once the solution in the second container 45 is exhausted.

Filtration levels can vary in all of the filter devices shown from the largest pore openings in the hydrophilic filter element to the finest pore size which will allow fluid flow. In the majority of fine pore filters these are supported on only one side and as thus designed to be unidirectional in flow. It is contemplated that in any of such configuration, a suitable back pressure check valve may be added similar to the valve shown at 25, FIG. 2, to eliminate the potential danger of rupturing the membrane by pressure applied in the fluid path below the filter membrane.

It is contemplated that there could be the placement of additional Y-connector sites such as shown at 27 onto the main conduit 23 to provide for the addition of other I.V. sets should this be needed for the administration of additional solutions or to provide a secondary source for the secondary solution. Additional flow control devices or clamps would be employed with additional filters and additional check valves or other configurations which effectively and safely control the flow of liquids and prevent the flow of air into the system.

With the inclusion into the secondary I.V. set of a positive air flow control device, such set could be utilized with a primary I.V. set without a hydrophilic/hydrophobic filter or hydrophilic filter such as above described with respect to FIGS. 2, 3 and 4. Some form of air check system is absolutely required for the safe operation of the present I.V. sets.

It should be understood that the spikes or connectors may be vented or unvented as is well known in the art. The drip chambers described herein are optional. Further the distal end of the set provided with the needle adapter 31 may be connected to needle, catheter, to another set or directly to the patient as is known in the art. The term "flow control device" may include all types of flow restriction devices both mechanical and electrical-mechanical such as a pump.

Having described my invention reference should now be had to the following claims.

I claim:

1. In an intravenous set including a standard, a first container suspended from the standard and containing a first solution at a predetermined first level, a connector extending into the container, a first tubing depending from said connector and at its free end having means for connecting the set to a needle, catheter, to another set or directly to the veins of a patient, a connector site interposed in said first tubing adapted for the reception of a second solution from a second container suspended from said standard, the second solution being above said first level, a check valve in said first tubing above said connector site, and a first adjustable flow control clamp on said first tubing below said connector site for controlling the rate of flow of the second solution; the improvement comprising a second adjustable flow control clamp on said first tubing above said connector site, said second flow control clamp being preset for automatically initiating and controlling the rate of flow of the first solution from the first container after termination of the flow of the second solution from the second container, said first and scond adjustable flow control clamps being generally set at different flow rates; and a device in said first tubing below said connector site for preventing any air entering said first tubing through said connector site and the second container from continuing to the patient.

2. In the intravenous set of claim 1, said device comprising a dual hydrophilic and hydrophobic filter in said first tubing below the connector site, for the filtration of all solutions, and for venting to atmosphere any possible air entering said first tubing through the second container.

3. In the intravenous set ofclaim 1 wherein said first container has a stopper, and a drip chamber attached to said connector, said connector extending through stopper into said first container.

4. In the intravenous set of claim 2, the second container and second solution comprising a secondary intravenous set including a stopper, a drip chamber having a connector projected through the latter stopper, a second tubing at one end depending from the latter drip chamber and at its other end connected into said connector site.

5. In the intravenous set of claim 4, a third adjustable flow control clamp interposed in said second tubing intermediate its ends, said third adjustable flow control clamp being normally wide open, 6. In an intravenous set, a first container adapted to be suspended from a standard and containing a first solution at a predetermined first level, a connector extending into the container, a first tubing depending from said connector and at its free end having means for connecting the set to a needle, catheter, to another set or directly to the veins of a patient, a connector site interposed in said first tubing adapted for the reception of a second solution from a second container adapted to be suspended from a standard, the second solution being above said first level a check valve in said first tubing above said connector site, and a first adjustable flow control clamp on said first tubing below said connector site for controlling the rate of flow of the second solution; the improvement comprising a second adjustable flow control clamp on said first tubing above said connector site, said second flow control clamp being preset for automatically initiating and controlling the rate of flow of the first solution from the first container after termination of the flow of the second solution from the second container, said first and second adjustable flow control clamps being generally set at different flow rates; the second container and the solution therein comprising a secondary intravenous set including a stopper, a drip chamber having a connector projected through the latter stopper, a second tubing at one end depending from the latter drip chamber and ar its other end connected into the connector site; and a filter means interposed in the second tubing intermediate its ends preventing passage of air beyond said filter means and into said first tubing.

7. In the intravenous set of claim 6, said filter means being a dual hydrophilic filter for the filtration of the second solution and for venting to atmosphere any possible air entering the second tubing from the second container.

8. In the intravenous set of claim 6, said filter means being a hydrophilic filter within the drip chamber depending from the second container.

9. In an intravenous set, a first container adapted to be suspended from a standard and containing a first solution at a predetermined first level, a connector extending into the container, a first tubing depending from said connector and at its free end having means for connecting the set to a needle, catheter, to another set or directly to the veins of a patient, a connector site interposed in said first tubing adapted for the reception of a second solution from a second container suspended from a standard, the second solution being above said first level, a check valve in said first tubing above said connector site, and a first adjustable flow control clamp on said first tubing below said connector site for the controlling the rate of flow of the second solution; the improvement comprising a second adjustable flow control clamp on said first tubing above said connector site, said second flow control clamp being preset for automatically initiating and controlling the rate of flow of the first solution from the first container after termination of the flow of the second solution from the second container, said first and second adjustable flow control clamps being generally set at different flow rates; the second container and solution comprising a secondary intravenous set including a stopper, a drip chamber having a connector projected through the latter stopper, a second tubing at one end depending from the latter drip chamber and at its other end connected into the connector site, and a floatable ball check nested within the drip chamber corresponding to the second container for preventing the passage of air therefrom when the solution therein is exhausted.

10. In the intravenous set of claim 1, the second container and solution therein comprising a secondary intravenous set including a stopper, a drip chamber having a connector projected through the latter stopper, a second tubing at one end depending from the latter drip chamber and at its other end connected into the connector site, an air valve closure tip normally spaced above the connector which depends from the second container; a slide shaft axially depending from said air valve closure tip, and loosely extending down into the second drip chamber connector; and a float upon the other end of the slide shaft normally immersed within fluid within the latter drip chamber connector and for permitting the flow of fluids therethrough, said air valve closure tip adapted to drop relative to said stopper for closing off air flow therethrough upon the falling of the solution within said second drip chamber to a predetermined level and for preventing the passage of air therethrough.

11. An intravenous set having on one end thereof a connector adapted to be attached to a container having a first solution at a predetermined first level, and having on the other end thereof a connection means for connecting the set to a needle, catheter, to another set or directly to the veins of a patient, a first tubing depending from said connector to said connection means, a connector site in said first tubing adapted for the reception of a second solution from a second container having a level above said first level, a check valve in said first tubing above said connector site, a first adjustable flow control device on said first tubing below said connector site adapted for controlling the rate of flow of the second solution, and a second adjustable flow control device on said first tubing on the upstream side of said connector site for automatically initiating and controlling the rate of flow of the first solution from the first container generally after termination of the flow of the second solution from the second container, said first and second flow control devices being generally set at different flow rates; and filter means for venting to atmosphere any air possibly entering the tubing through the second container and to prevent any air entering the tubing through the second container from continuing to the patient.

12. The intravenous set defined in claim 11 wherein said second flow control device is located in said first tubing on either side of said check valve.

13. The intravenous set defined in claim 11 wherein means is provided for venting said tubing.

14. The intravenous set defined in claim 11 wherein means is provided for preventing air from entering said first tubing.

15. The intravenous set defined in claim 11 wherein said connector is in the form of a spike.

16. The intravenous set defined in claim 15 wherein said spike is vented.

17. The intravenous set defined in claim 15 wherein said spike is unvented.

18. The intravenous set defined in claim 11 wherein said set has a drip chamber and said connector is in the form of a spike connected to said drip chamber.

19. The intravenous set defined in claim 11 wherein said flow control devices are of the roller clamp type.

20. The intravenous set defined in claim 11 wherein said flow control devices are of the slide clamp type.

21. The intravenous set defined in claim 11 wherein said flow control devices are of the screw clamp type.

22. The intravenous set defined in claim 11 wherein said connector site is in the form of a y-type injection site.

23. The intravenous set defined in claim 11 wherein said filter means is provided in said first tubing, said filter means being in the form of a hydrophilic-hydrophobic filter.

24. The intravenous set defined in claim 23 wherein said filter is located downstream of said check valve on either side of said first flow control device.

25. The intravenous set defined in claim 11 wherein said filter means is provided in said first tubing, said filter means being in the form of hydrophilic filter.

26. The intravenous set defined in claim 11 wherein the second container and the second solution comprises a secondary intravenous set, a second connector attached to the second container and a second tubing at one end depending from said second connector and at its other end connected into said connector site.

27. The intravenous set defined in claim 26 wherein a third adjustable flow control device is interposed in said second tubing intermediate its ends, said third device being normally wide open.

28. The intravenous set defined in claim 26 wherein said secondary set includes a stopper, a second drip chamber to which said second connector is connected through said stopper, said second tubing at said one end depending from said second drip chamber, and said filter means being interposed in said second tubing intermediate its ends.

29. The intravenous set defined in claim 28 wherein said filter means being a hydrophilic and hydrophobic filter for the filtration of the secondary solution and for venting to atmosphere any possible air entering the second tubing from the second container.

30. The intravenous set defined in claim 28, wherein said filter means is in the form of a hydrophilic filter within the drip chamber depending from said second container.

31. In a set for the sequential administration of medical liquids to a patient, said set including:
- a primary tube for the flow of a primary medical liquid therethrough and including a primary valve for controlling the flow of liquid through said primary tube,
- a secondary tube for the flow of a secondary medical liquid therethrough,
- a common tube having its distal end in fluid communication with the proximal ends of said primary and secondary tube and its proximal end open for the flow of liquid therefrom to form a primary liquid flow path comprising said primary tube and said common tube and a secondary liquid flow path comprising said secondary tube and said common tube, the improvement which comprises:
- a secondary flow control means in said secondary liquid flow path for adjusting the flow rate of said secondary liquid therethrough,
- a primary flow control means on said primary tube for adjusting the flow rate of said primary liquid through said primary flow path to a rate independent of the flow rate of said secondary liquid through said secondary liquid flow path, and
- an air barrier means within said secondary liquid flow path substantially impervious to air but permitting liquid flow there through while said set is in use and preventing the flow of air therethrough after said secondary liquid has been depleted, whereby, following administration of said secondary liquid, flow of said primary liquid may be resumed at the preset rate without adjustment of said primary or said secondary flow control means.

32. The set defined in claim 31, wherein said air barrier comprises a hydrophilic membrane disposed in a housing having an inlet and outlet in fluid communication with said secondary liquid flow path.

33. The set defined in claim 31, wherein said air barrier comprises a mechanical valve disposed in a housing having an inlet and outlet in fluid communication with said secondary liquid flow path.

34. The set defined in claim 33, wherein said mechanical valve is a float valve.

35. The set defined in claim 31, wherein said air barrier is located between the ends of said secondary tube.

36. The set defined in claim 31, wherein said air barrier is located between the ends of said common tube.

37. The set defined in claim 32, wherein said housing includes an air vent.

38. The set defined in claim 37, wherein said air vent is covered by a hydrophobic membrane.

39. the set defined in claim 31, wherein said primary tube further includes a primary piercing pin at its distal end for insertion into a container for a primary medical liquid and a drip chamber for forming drops of said primary liquid.

40. The set defined in claim 39, wherein said secondary tube further includes a secondary piercing pin at its distal end for insertion into a container for a secondary medical liquid, and a drip chamber for forming drops of said secondary liquid.

41. The set defined in claim 39 or 40, wherein said piercing pins and drip chambers are integral.

42. The set defined in claim 39 or 40, wherein said piercing pins have integral air vents.

43. The set defined in claim 31, wherein said secondary flow control means is on said common tube.

44. The set defined in claim 31, wherein said primary flow control means is on the distal side of said primary valve and said primary valve is further characterized as a one-way valve that allows said primary liquid to flow towards said common tube, but prevents the flow of said secondary liquid into said primary tube.

45. In a gravitational flow system for the sequential administration of medical liquids to a patient, said system including:
- a primary container suspended in space for containing a primary medical liquid,
- a primary tube having its distal end in fluid communication with said primary container,
- a secondary container suspended in space at a height greater than that of said primary container for containing a secondary medical liquid,
- a secondary tube having its distal end in fluid communication with said secondary container,
- a common tube having its distal end in fluid communication with the proximal ends of said primary and secondary tubes and its proximal end open for the flow of liquid therefrom to form a primary liquid path comprising said primary tube and said common tube and a secondary liquid flow path comprising said secondary tube and said common tube, and
- a primary valve in said primary tube which allows primary liquid to flow from said primary container whenever the height of said primary liquid is greater than or equal to the height of said secondary liquid in said system and which prevents primary liquid from flowing from said primary container whenever the height of said primary liquid is less than the height of said secondary liquid in said system, the improvement which comprises:
    - an air barrier means within said secondary liquid flow path substantially impervious to air but permitting liquid flow there through while said system is in use and preventing the flow of air therethrough after said secondary liquid has been depleted,
    - secondary flow control means in said secondary liquid flow path for adjusting the flow rate of said secondary liquid therethrough, and
    - primary flowing control means on said primary tube for adjusting the flow of said primary liquid through said primary liquid flow path at a rate independent of the flow rate of said secondary liquid through said secondary liquid flow path, whereby following administration of said secondary liquid, flow of said primary liquid may be resumed at the present rate without adjustment of said primary or said secondary flow control means.

* * * * *